US005482679A

United States Patent [19]
Dijkstra et al.

[11] Patent Number: 5,482,679
[45] Date of Patent: Jan. 9, 1996

[54] DEVICE FOR DETERMINING THE WOBBE INDEX OF A GAS MIXTURE

[75] Inventors: Kees Dijkstra; Hermanus M. Verbeek, both of Groningen, Netherlands

[73] Assignee: N.V. Nederlandse Gasunie, Netherlands

[21] Appl. No.: 257,675

[22] Filed: Jun. 8, 1994

[30] Foreign Application Priority Data

Jun. 8, 1993 [NL] Netherlands .......................... 9300984

[51] Int. Cl.⁶ .................................................. G01N 31/12
[52] U.S. Cl. .............................. 422/94; 422/98; 374/36; 374/37; 137/7; 137/100; 73/23.2; 73/30.01
[58] Field of Search ......................... 422/94, 98; 374/36, 374/37; 137/7, 100; 73/23.2, 30.01

[56] References Cited

U.S. PATENT DOCUMENTS

| | | | |
|---|---|---|---|
| 4,318,868 | 3/1982 | Showwalter et al. | 261/41 D |
| 4,359,284 | 11/1982 | Kude et al. | 374/37 |
| 4,380,400 | 4/1983 | Searle | 374/37 |
| 4,382,698 | 5/1983 | Szonntagh | 374/37 |
| 4,384,792 | 5/1983 | Sommers et al. | 374/36 |
| 4,634,559 | 1/1987 | Eckert | 261/76 |
| 4,941,345 | 7/1990 | Altemark et al. | 73/23.2 |
| 5,288,149 | 2/1994 | Meyer | 374/36 |
| 5,329,955 | 7/1994 | Gensler et al. | 137/7 |

*Primary Examiner*—Robert J. Warden
*Assistant Examiner*—N. Bhat
*Attorney, Agent, or Firm*—Cushman Darby & Cushman

[57] ABSTRACT

Device for determining the Wobbe index of a first gas mixture, including a Wobbe index meter having a mixing chamber, and a feed system for supplying a first gas mixture and an oxidation gas to the mixing chamber of the Wobbe index meter. The feed system includes structure for supplying the first gas mixture to the mixing chamber via a first number of openings, structure for supplying an oxidation gas to the mixing chamber via a second number of openings, structure for keeping a constant ratio between the a quantity of first gas mixture and the a quantity of oxidation gas supplied to the mixing chamber, structure for burning the second gas mixture formed in the mixing chamber and structure for determining the oxygen content of the combustion gas obtained after combustion. In accordance with the invention, the ratio of the diameters of the openings for the supply of the first gas mixture and the oxidation gas to the mixing chamber is chosen such that the Reynolds numbers of the flows of the first gas mixture and the oxidation gas through the openings are equal, and such that the number of openings is determined by the desired ratio of the flow rates of the first gas mixture and the oxidation gas.

4 Claims, 1 Drawing Sheet

5,482,679

DEVICE FOR DETERMINING THE WOBBE INDEX OF A GAS MIXTURE

The invention relates to a device for determining the Wobbe index of a first gas mixture, comprising a mixing chamber, means for supplying the gas mixture to the mixing chamber via a first number of openings, means for supplying an oxidation gas to the mixing chamber via a second number of openings, means for keeping a constant ratio between the quantity of first gas mixture and the quantity of oxidation gas supplied to the mixing chamber, means for burning the second gas mixture formed in the mixing chamber, and means for determining the oxygen content of the flue gas obtained after combustion.

For the determination of the Wobbe index of gas mixtures various types of devices are known. A number of them are described in Dutch patent applications 8802336, 8901660 and 9000449.

With these known devices, the first gas mixture of which the Wobbe index must be determined is mixed with an oxidation gas such as air. This mixing takes place in a mixing chamber which is connected on the one hand to a supply of the first gas mixture and on the other hand to a supply of an oxidation gas such as air. It is attempted to obtain and maintain a constant ratio between the quantities of supplied first gas mixture and oxidation gas. The obtained second gas mixture is conveyed from the mixing chamber to a combustion chamber where it is burned. The oxygen content of the combustion gas obtained in this way is determined. Use is made of a so-called lambda probe for the determination of the oxygen content of the flue gas. In general, this will be done using excess air.

For the determination of the Wobbe index then various methods can be used. A first method involves keeping the measured value of the oxygen content constant. The signal from the lambda probe is then used to regulate the supply of either the first gas mixture or of the oxidation gas, so that the resulting oxygen content remains constant. The Wobbe index can then be determined through the set values of either the flow rate of the first gas mixture or the flow rate of the oxidation gas. This method ensures that the lambda probe is always used in the same operating range so that, when provisions are present for keeping the temperature constant, the characteristic and particularly the ageing and consequently the change in the characteristic of the lambda probe have no influence on the measured value of the Wobbe index. With other methods, the oxygen content measured by the lambda probe is directly converted into a Wobbe index value.

If the second method is used, it is important to ensure a constant ratio between the quantity of supplied first gas mixture and the quantity of supplied oxidation gas. For that purpose, a suitable arrangement will generally be present for matching the pressure of the first gas mixture in the feed line to the mixing chamber and the pressure of the oxidation gas in the feed line to the mixing chamber. As a rule an effort will be made to work with equal pressures in the two feed lines since this is technically the simplest solution, but it is of course possible to work with constant pressure ratios. Furthermore it is important to make the temperature of the first gas mixture and the air equal in order to maintain a constant gas-air ratio.

In practice it is found that the quantity of oxidation gas to be supplied to the mixing chamber must be considerably larger than the quantity of first gas mixture. In the case of natural gas, for example, the quantity of air must be approximately 8 to 10 times the quantity of natural gas to achieve stoichiometric combustion. In the case of combustion with excess oxygen this must be even higher.

As a result of this required air-gas ratio, the diameter of the opening for the supply of the oxidation gas will have to be larger than the diameter of the opening for the supply of the first gas mixture, if the numbers of openings are equal. This difference in diameter has an influence on the flow pattern through the openings and under changing conditions (pressure, temperature) the flow patterns will not change in the same way, causing the air-gas ratio in the mixing chamber to change. The above-mentioned effect can be described with the Reynolds number. By adapting the diameter of the opening for the oxidation gas to the diameter of the opening for the first gas mixture, the invention ensures that the Reynolds numbers of the two flows are equal and that the obtained air-gas ratio in the mixing chamber remains constant. The number of openings for the supply of the oxidation gas must accordingly be made greater than the number of openings for the supply of the first gas mixture. The exact number of openings is determined by the required air-gas ratio.

Preferably, use is made of one feed opening for the first gas mixture and a number of feed openings for the oxidation gas. When a more or less constant pressure is maintained in the feed line of the first gas mixture, which in practice is generally the case, the dimension of the opening can be determined such that such a quantity of first mixture flows through it as is adequate for the determination of the Wobbe index using this method, without large quantities of gas mixture having to be consumed.

Preferably the number of feed openings for the oxidation gas is chosen such that the quantity of oxidation gas supplied is greater than necessary for stoichiometric combustion of the second gas mixture.

In this way, the oxygen content in the flue gas measured by the lambda probe can be used directly for the determination of the Wobbe index.

DETAILED DESCRIPTION OF THE INVENTION

Other characteristics and advantages of the invention will become evident from the following description, in which reference is made to the attached schematic perspective drawing showing the feed section for the different gases flowing to a mixing chamber.

For a more detailed description of possible embodiments of a Wobbe meter, the reader is referred to the above-mentioned Dutch patent applications 8802336, 8901660 and 9000449.

The feed system described below can be used to supply the gases to the mixing chamber used in these known Wobbe meters.

Figure 2:
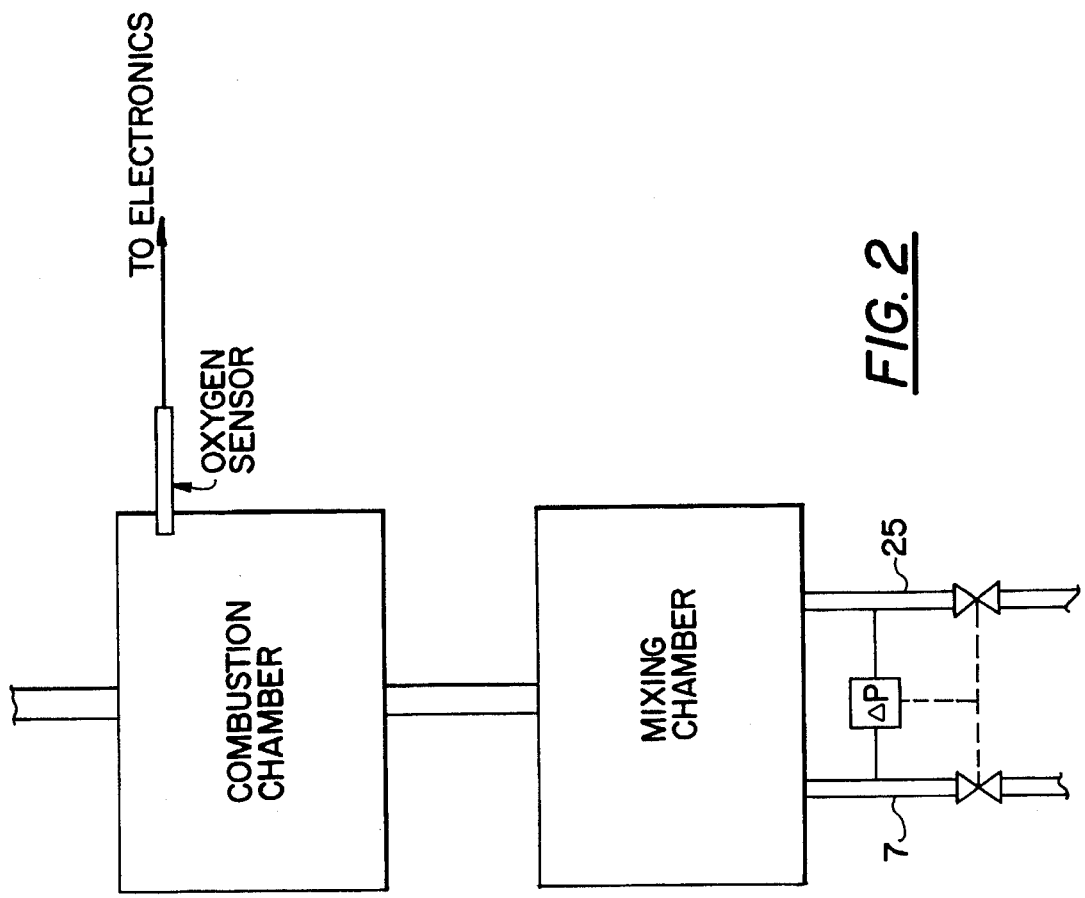
FIG. 2 is a schematic view of a mixing chamber in accordance with the invention in relation to a combustion chamber and oxygen sensor of a Wobbe index meter.
Figure 1:
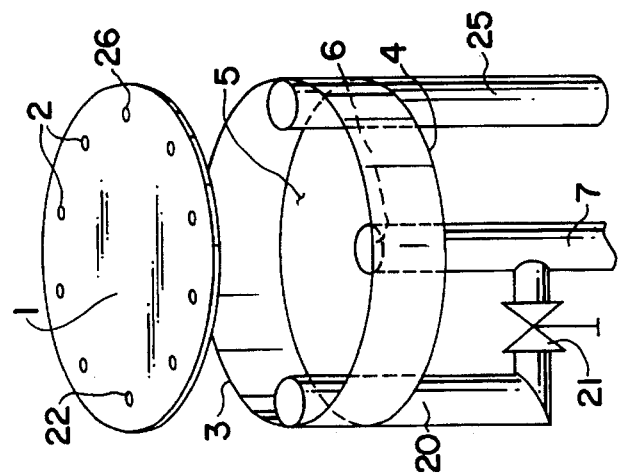
FIG. 1 is a perspective view of a feed system for supplying gases to a mixing chamber, provided in accordance with the principles of the present invention.

The feed system as shown in the FIG. 1 comprises a circular plate 1 which is provided with a number of holes 2 around its circumference. The plate 1 forms a part of the mixing chamber and forms a cover for a cylindrical space 5 formed by a wall 3 and a circular baseplate 4. In the circular plate 4, a central opening 6 is provided which is connected via a line 7 to a supply of oxidation gas such as air. Through the wall 4 passes a pipe 20 which extends up to the plate 1 and is connected via a valve 21 to line 7. An opening 22 has been made in the plate 1 above the end of the pipe 20. On the other side, a second pipe 25 passes in the same way through the plate 4, which pipe is connected to a supply of gas of which the Wobbe index must be determined. The pipe 25 is connected to the mixing chamber via an opening 26 in the plate 1.

In the reproduced embodiment, the feed system for the oxidation gas is therefore connected to the mixing chamber via eight openings 2 and possibly also via opening 22 depending on the position of the valve 21, while the feed system for the gas to be measured is connected to the mixing chamber via opening 26.

The diameter of opening 26 is chosen such that at the prevailing pressure ratios the gas flow rate is sufficient to perform a stable measurement. A good value for the gas flow rate is for example 60 liters per hour. The diameter of the opening 26 and the thickness of the plate 1 are of the same order of magnitude, so that none of the flow phenomena that are typical of pipes occurs.

In order to eliminate or limit the influence of a change in the flow patterns of the flows of first gas mixture and oxidation gas on the obtained air-gas ratio it is necessary to choose the diameter of the openings for the supply of oxidation gas such that the Reynolds numbers for the two flows are equal.

To this end, the following calculation can be performed, in which
$\Phi$=flow rate
v=velocity
$\Delta$p=pressure drop
$\rho$=density
d=diameter and
$\eta$=viscosity the diameter of the gas opening 26 and the gas flow rate are known. According to formulas (1) and (2) the pressure drop across the gas opening follows from this.

$$\Phi_{gas} = v_{gas} * \text{area of gas opening} \quad (1)$$

$$\Delta P_{gas} = \tfrac{1}{2}\rho_{gas} * v^2 \text{ gas} \quad (2)$$

given the above-mentioned provisions with respect to the pressures in the feed lines of first gas mixture and oxidation gas, the pressure drop across the air openings 2 is also known now:

$$\Delta P_{air} = \Delta P_{gas}$$

$$v_{air} = \sqrt{\Delta P_{air}/\tfrac{1}{2}P_{air}} \quad (3)$$

the Reynolds number is defined according to:

$$Re = \rho v d/\eta \quad (4)$$

the ratio of the diameters of the openings for the supply of first gas mixture and oxidation gas is obtained by making the Reynolds numbers equal:

$$Re_{gas} = \frac{\rho_{gas} V_{gas} d_{gas}}{\eta_{gas}} = Re_{air} = \frac{\rho_{air} V_{air} d_{air}}{\eta_{air}} \quad (5)$$

or $$\frac{d_{gas}}{d_{air}} = \frac{\rho_{air}}{\rho_{gas}} * \frac{V_{air}}{V_{gas}} * \frac{\eta_{gas}}{\eta_{air}}$$

from this the diameter of the opening for the supply of the oxidation gas can be calculated. If the diameter of the opening is known, the flow rate through one opening is also known and by reference to the total quantity of oxidation gas required the required number of openings for the supply of oxidation gas can then be determined. (Since the viscosity and density of gas change with the composition, average values must be entered in formulas 2 and 5 for the density and viscosity of the first gas mixture).

The opening 22 has the same dimensions as the openings 2 and enables the Wobbe meter to be calibrated using only one calibration gas instead of the customary two calibration gases. "Calibration gas" here means a gas with known Wobbe index.

The calibration method used is as follows. With valve 21 in the closed position, a calibration gas is supplied via line 25 and an oxidation gas via line 7. In this way, one point of the calibration curve of oxygen content vs. Wobbe index is fixed. This measurement is subsequently repeated with the valve 21 in the open position. A situation is therefore simulated in which a second calibration gas with a lower Wobbe index is supplied to the meter.

Since the opening 22 is equal to the openings 2, it is known how much extra oxidation gas is supplied to the mixing chamber and the Wobbe index of the simulated second calibration gas and the second point of the calibration curve can be determined. From this the calibration curve of the Wobbe meter is known.

We claim:

1. A Wobbe index meter for use in determining the Wobbe index of a first gas mixture, comprising a combustion chamber, a mixing chamber, a feed system for supplying a first gas mixture and an oxidation gas to the mixing chamber, said feed system including:

means operatively coupled to the mixing chamber for supplying the first gas mixture to the mixing chamber via a first number of openings, and means operatively coupled to the mixing chamber for supplying an oxidation gas to the mixing chamber via a second number of openings, means for keeping a constant ratio between a quantity of first gas mixture and a quantity of oxidation gas supplied to the mixing chamber, means for burning in said combustion chamber a second gas mixture formed in the mixing chamber, and means operatively coupled to the combustion chamber for determining the oxygen content of a combustion gas therein obtained after combustion, wherein the ratio of the diameters of the openings for the supply of the first gas mixture and the oxidation gas to the mixing chamber are predetermined to ensure that the Reynolds numbers of the first gas mixture and the oxidation gas flowing through the openings are equal, and wherein the number of openings is pre-determined by the desired ratio of the flow rates of first gas mixture and the oxidation gas whereby, the determined oxygen content of the combustion gas can be used to directly determine the Wobbe index of the first gas mixture.

2. Device according to claim 1, wherein one feed opening is used for the first gas mixture and a number of feed are used for the oxidation gas.

3. Device according to claim 2, wherein the number of feed openings for the oxidation gas is greater than necessary for stoichiometric combustion of the second gas mixture.

4. A device as in any one of claims 1–3 further comprising a value for shutting-off one of the feed openings for one of the gas flows for which several feed openings are present.

* * * * *